US009629929B2

(12) United States Patent
Lötvall et al.

(10) Patent No.: US 9,629,929 B2
(45) Date of Patent: *Apr. 25, 2017

(54) EXOSOME TRANSFER OF NUCLEIC ACIDS TO CELLS

(71) Applicant: Codiak Biosciences, Inc., Woburn, MA (US)

(72) Inventors: Jan Lötvall, Mölnlycke (SE); Hadi Valadi, Göteborg (SE)

(73) Assignee: CODIAK BIOSCIENCES, INC., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/750,457

(22) Filed: Jun. 25, 2015

(65) Prior Publication Data

US 2015/0290343 A1    Oct. 15, 2015

Related U.S. Application Data

(63) Continuation of application No. 11/799,148, filed on Apr. 30, 2007, now Pat. No. 9,085,778.

(60) Provisional application No. 60/797,149, filed on May 3, 2006.

(51) Int. Cl.
*A61K 48/00* (2006.01)
*C12N 15/87* (2006.01)
*C12N 15/113* (2010.01)

(52) U.S. Cl.
CPC ........ *A61K 48/0033* (2013.01); *C12N 15/113* (2013.01); *C12N 15/87* (2013.01); *A61K 48/00* (2013.01); *C12N 2310/14* (2013.01); *C12N 2320/32* (2013.01)

(58) Field of Classification Search
CPC ................................ A61K 48/00; C12N 15/87
See application file for complete search history.

(56) References Cited

U.S. PATENT DOCUMENTS

| | | | |
|---|---|---|---|
| 6,812,023 | B1 | 11/2004 | Lamparski et al. |
| 7,198,923 | B1 | 4/2007 | Abrignani et al. |
| 7,405,292 | B2 | 7/2008 | Finkel et al. |
| 2004/0028692 | A1 | 2/2004 | Zitvogel et al. |
| 2004/0197314 | A1 | 10/2004 | Delcayre et al. |
| 2007/0298118 | A1 | 12/2007 | Lotvall et al. |

FOREIGN PATENT DOCUMENTS

| | | |
|---|---|---|
| CN | 1265038 A | 8/2000 |
| CN | 1325441 A | 12/2001 |
| WO | WO-00/28001 A1 | 5/2000 |
| WO | WO-01/36601 A1 | 5/2001 |
| WO | WO-02/082904 A2 | 10/2002 |
| WO | WO 03/011330 A1 | 2/2003 |
| WO | WO 03/011660 A1 | 2/2003 |
| WO | WO-03/016522 A2 | 2/2003 |
| WO | WO-03/044166 A2 | 5/2003 |
| WO | WO-2005/121369 A2 | 12/2005 |
| WO | WO-2010/119256 A1 | 10/2010 |

OTHER PUBLICATIONS

Chinese Office Action dated Oct. 30, 2012 issued in Chinese Patent Application No. 2007800154690—English Translation Only.
Couzin, J., et al. (2005), "The Ins and Outs of Exosomes", Science, 308: 1862-1863.
European Communication dated Jun. 17, 2013 issued in European Patent Application No. 07 748 459.0.
European Communication dated Jun. 27, 2012 issued in European Patent Application No. 07 748 459.0.
European Communication dated Jul. 6, 2011 issued in European Patent Application No. 07 748 459.0.
European Examination Report and Supplemental Search Report dated Oct. 8, 2010 issued in European Patent Application No. 07 748 459.0, 7 pages.
Gehl, J. (2003), "Electroporation: theory and methods, perspectives for drug delivery, gene therapy and research" Acta Physiol Scand, 177: 437-447.
Office Action dated Dec. 17, 2010 issued in U.S. Appl. No. 11/799,148.
Office Action dated Apr. 2, 2010 issued in U.S. Appl. No. 11/799,148.
Office Action dated Mar. 26, 2014 issued in U.S. Appl. No. 11/799,148.
Office Action dated Sep. 29, 2010 issued in U.S. Appl. No. 11/799,148.
Office Action dated Sep. 3, 2009 issued in U.S. Appl. No. 11/799,148.
Office Action dated Nov. 7, 2014 issued in U.S. Appl. No. 11/799,148.
Ratajczak, J. et al. (2006), "Embryonic stem cell-derived microvesicles reprogram hematopoietic progenitors: evidence for horizontal transfer of mRNA and protein delivery", Leukemia, 20: 847-856.
Baj-Krzyworzeka, M. et al., "Tumour-Derived Microvesicles Carry Several Surface Determinants and mRNA of Tumour Cells and Transfer Some of These Determinants to Monocytes," Cancer Immunol. Immunother., 2006, pp. 808-818, vol. 55.
Delcayre, A. et al., "Exosomes as Novel Therapeutic Nanodevices," Current Opinion in Molecular Therapeutics, 2006, pp. 31-38, vol. 8, No. 1.
European Extended Search Report, European Application No. 07748459.0, Oct. 18, 2010, 8 pages.
European Summons to Attend Oral Proceedings Pursuant to Rule 115(1) EPC, European Application No. 07748459.0, Apr. 24, 2014, 7 pages.
European Extended Search Report, European Application No. 15158949.6, Jul. 13, 2015. 9 pages.
European Examination Report, European Application No. 15158949.6, Jun. 7, 2016, 4 pages.
Lederberg J., "The Transformation of Genetics by DNA: An Anniversary Celebration of Avery, MacLeod and McCarty (1944)," Genetics, Feb. 1994, pp. 423-426, vol. 136, No. 2.

(Continued)

*Primary Examiner* — Jon E Angell
(74) *Attorney, Agent, or Firm* — Fenwick & West LLP

(57) ABSTRACT

Methods for introducing nucleic acids to cells via exosomes for use in gene modulation and therapy, such as for gene silencing and to introduce genetic material into cells to compensate for abnormal genes or to induce or repress a process in the recipient cell.

19 Claims, No Drawings

(56) References Cited

OTHER PUBLICATIONS

Luo, Z-B. et al., "Immunotherapy of Dendritic Cells and Its Exosomes Transfected with mRNA of Gastric Cancer Cells in Tumor-Carried Mice," 2004, World Chin. J. Digestol., Jan. 2004, pp. 9-12, vol. 12, No. 1.
PCT International Search Report, PCT Application No. PCT/SE2007/050298, Sep. 14, 2007, 6 pages.
PCT Written Opinion, PCT Application No. PCT/SE2007/050298, Sep. 14, 2007, 9 pages.
Ponsaerts, P. et al., "Editorial: Modulation of Cellular Behavior by Exogenous Messenger RNA," Leukemia, 2006, pp. 767-769, vol. 20.
Raposo, G. et al., "B Lymphocytes Secrete Antigen-Presenting Vesicles," J. Exp. Med., Mar. 1996, pp. 1161-1172, vol. 183.
Razin, E. et al., "Interleukin 3: A Differentiation and Growth Factor for the Mouse Mast Cell That Contains Chondroitin Sulfate E Proteoglycan", The Journal of Immunology, Mar. 1984, pp. 1479-1486, vol. 132, No. 3.
Simpson, R.J. et al., "Extracellular Microvesicles: The Need for Internationally Recognised Nomenclature and Stringent Purification Criteria," Proteomics & Bioinformatics, 2012, 1 page, vol. 5, No. 2.
Valadi, H. et al., "Exosome-Mediated Transfer of mRNAs and microRNAs is a Novel Mechanism of Genetic Exchange Between Cells," Nature Cell Biology, Jun. 2007, pp. 654-659, vol. 9, No. 6.
Wahlgren, J. et al., "Plasma Exosomes Can Deliver Exogenous Short Interfering RNA to Monocytes and Lymphocytes," Nucleic Acids Research, 2012, 12 pages, vol. 40, No. 17.
European Examination Report, European Application No. 15158949.6, Oct. 19, 2016, 6 pages.
Chinese First Office Action, Chinese Application No. 201511027801.8, Dec. 7, 2016, 21 pages.

EXOSOME TRANSFER OF NUCLEIC ACIDS TO CELLS

CROSS-REFERENCE TO RELATED APPLICATIONS

This present application is a continuation of pending U.S. application Ser. No. 11/799,148 filed on 30 Apr. 2007, which claims the benefit of U.S. provisional application Ser. No. 60/797,149 filed on 3 May 2006. Each of the above-referenced applications are incorporated herein by reference to their entirety.

BACKGROUND OF THE INVENTION

Field of the Invention

The present invention is based on the unexpected findings that exosomes released to the extracellular milieu can carry selective RNA from the parental cells. This can, according to this invention, be used to transfer genetic material to recipient cells by exosomes. By transferring nucleic acids to recipient cells, exosomes affect another cell's (recipient cells) protein machinery and thus protein content, and the invention demonstrates for the first time that nucleic acids, for example RNA and DNA, deliberately can be transferred between the cells or organs using exosomes, and can thus be utilized for gene modulation and therapy in mammalian cells.

Description of the Related Art

Exosomes are small membrane vesicles of endocytic origin that are released into the extracellular environment following fusion of multivesicular bodies with the plasma membrane. The size of exosomes ranges between 30 and 100 nm in diameter. Their surface consists of a lipid bilayer from the donor cell's cell membrane, and they contain cytosol from the cell that produced the exosome, and exhibit membrane proteins from the parental cell on the surface.

Exosomes exhibit different composition and function depending on the cell type from which they are derived. There are no "exosome-specific" proteins; however several proteins identified in these vesicles are associated with endosomes and lysosomes reflecting their origin. Most exosomes are enriched in MHC I and II (major histocompatibility complex I and II; important for antigen presentation to immunocompetent cells such as T-lymphocytes), tetraspanins, several heat shock proteins, cytoskelatal components such as actins and tubulins, proteins involved in intracellular membrane fusion, signal transduction proteins and cytosolic enzymes.

Exosomes are produced by many cells including epithelial cells, B and T lymphocytes, mast cells (MC) as well as dendritic cells (DC). In humans, exosomes have been found in blood plasma, urine, bronchoalveolar lavage fluid, intestinal epithelial cells and tumor tissues.

All functions of exosomes have not been elucidated, but data strongly indicates they mediate communication between cells. This communication could take place in different ways. First, exosomes could bind to cell surface receptor in a similar way as cell to cell interaction. Second, exosomes could attach to the cell membrane and give the cells new receptors and properties. Thus, exosomes can also fuse with target cells and exchange membrane proteins and cytosol between two cell types.

We have put extra effort into understanding the content and biological function of exosomes specifically released by mast cells. In proteomic assays we have found that these exosomes contain a larger number of proteins than previously understood. However, the unique finding from our research is that we have discovered a substantial amount of selective RNA in exosomes from mast cells. Furthermore, use of different recipient cells displays an uptake of exosomal RNA indicating transfer of genetic material from exosomes into recipient cells, which in turn will lead to translation of specific protein in the target cells.

Considering the exosomal protein content and their capacity to communicate with different recipient cells, it is particularly useful to be able to modify the genetic content of exosomes in order to add or regulate a gene in recipient cells. The method using the exosomes' capacity of carrying specific genetic material and transferring it to recipient cells is described in this application. In this method, the recipient is affected in its function, as well as in its ability to stay alive, further develop, proliferate or mature.

The method is unique and different from any previous described methods. Several patents and patent applications use exosomes to influence the immune system through stimulatory or inhibitory function via exosomal protein interaction with immune cells, and for treatment of viral disease by influencing the immune system. It has been suggested that exosomal proteins can be modified by mutation to affect the immune system. However, no patent or patent application or any publicly available information that we have found describes or suggests use of exosomes to transfer genetic material or nucleic acids to cells.

SUMMARY OF THE INVENTION

The present invention discloses novel methods of delivering nucleic acid constructs by exosomes to cells. The invention method includes RNA and DNA constructs that are transferred into exosomes by using their parental cells (transformation, transfection, or modification of the parental cells), or using conventional methods for instance, transformation and transfection, to introduce nucleic acids directly into exosomes. The method of the invention is an excellent tool for gene therapy to introduce genetic material into recipient cells to compensate for abnormal genes or to introduce RNA or DNA that produces proteins that affect the function of the recipient cells or their ability to stay alive or develop or mature. For gene therapy, usually viruses or liposomes are used as vectors for transfer of genetic material, because they can deliver the new gene by infecting the cell. Use of exosomes has several advantages compared to conventional methods, and most importantly exosomes are derived from cells, and possibly even the recipient's own cells, and are thus not a foreign body for the immune system, avoiding adverse immune reactions. Exosomes are thus easily produced, isolated and modified for use in gene modulation and therapy.

Other objects and features of the inventions will be more fully apparent from the following disclosure and appended claims.

DETAILED DESCRIPTION OF THE INVENTION AND PREFERRED EMBODIMENTS THEREOF

Using exosome vesicles for transferring genetic material, nucleic acids, to the cytosol or nucleus of a cell as described in the invention herein, can treat inherited diseases, cellular or body dysfunctions, induce or repress cell death (apoptosis), change cellular ageing, induce tolerance, re-direct existing immune responses, change intracellular activity or cellular behaviour. It can also be used in all kinds of gene therapy of genetic disorders, malignant diseases or diseases involving immune cells or any other cell type in the body including vasculature, epithelial cells, interstitial cells, musculature, skeletal system, nervous system, liver cells, kidney cells, gut cells, lung cells, skin cells or any other cell in the body.

Genetic material that can be transferred by exosomes, described in the invention herein is: microRNA, mRNA, tRNA, rRNA, siRNA, regulating RNA, non-coding and coding RNA, DNA fragments, and DNA plasmids, including nucleic acids of any type. The methods of transferring the genetic material (constructs of DNA or RNA, or any type of nucleic acids) directly into exosomes are transformation, transfection and microinjection.

Genetically dissimilar exosomes can be isolated for further delivery to recipient cells using either their donor cells or by introducing specific nucleic acids into them. Different approaches for production of exosomes containing a set of genetic material are described below.

Different procedures for production of genetic dissimilar exosomes using the exosome producing cells for further delivery to recipient cells include:

(a) Exosomes from Different Donor Cells.

Exosomes containing different set of genetic material can be isolated from different donor cells (e.g. B and T lymphocytes, mast cells, and dendritic cells) for further delivery to recipient cells. Since the genotype of the donor cells are dissimilar, which is due to their role and environment, the isolated exosomes from different cell type give rise to exosomes with dissimilar genotypes.

(b) Exosomes from Different Conditions.

Growth of the exosome producing cells in a certain condition give rise to cellular changes, and subsequently to genetically modified exosomes. The exosomes can subsequently be used for transferring the set of nucleic acids to recipient cells.

(c) Exosomes from Different Human being or Disease.

Exosomes from different persons or diseases contain diverse set of nucleic acids. The genotype of the exosomes is different due to their donor cell's source and conditions. The exosomes with the unique set of nucleic acids can be isolated for further delivery of the nucleic acids to recipient cells.

(d) Exosomes from Genetically Modified Donor Cells.

Gene disruption or mutations in exosome producing cells give rise to genetically modified exosomes that can be used for delivery of their nucleic acids to recipient cells. Expression of any kind of nucleic acids present in exosomes can be influenced (erased or up/down regulated) by gene manipulation of the exosome producing cells. For instance, disruption of a gene in exosome producing cells results in a lack of corresponding mRNA in exosomes. Simultaneously, up or down regulation of a gene in exosome producing cells affects amount of corresponding mRNA in exosomes.

Specific nucleic acid construct(s) (cloned genes, DNA fragments and plasmids, microRNA, siRNA, coding and none coding DNA and RNA) can be transferred to recipient cells via genetic modified exosomes. The nucleic constructs can be manufactured using standard techniques e.g. cloning, isolation and amplification of RNA or DNA sequences, for further transformation into exosomes.

(a) Insertion of Specific Constructs into Exosomes Using their Donor Cells.

New constructs (RNA and DNA) can be introduced into exosomes using their donor cells. The nucleic acid constructs can be introduced into the donor cells (the exosome producing cells) and consequently by the intracellular functions the transcript or the constructed by itself will be translocated into exosomes.

(b) Insertion of Specific Constructs Directly into Exosomes.

Exosomes can be isolated from different origin, e.g. in vitro growing cells, human body, or cells originated from a human and animal. Genetic constructs of RNA or DNA can be introduced into these exosomes directly by using conventional molecular biology techniques such as in vitro transformation, transfection, and microinjection. The genetically modified exosomes can further be used for transferring their nucleic acids to recipient cells.

Methods for Production of Genetically Modified Exosomes

Transformation or transfection of genetic material into exosomes More generally the term transformation and transfection is used to describe mechanisms of DNA and RNA transfer in molecular biology and it was described for the first time 1944 by Oswald Avery, Colin MacLeod, and Maclyn McCarty (Lederberg J., Genetics. 1994 February; 136(2):423-6).

(a) Electroporation.

By this methods number of holes is made in cells/exosomes by briefly shocking them with and electric field of 100-200 V/cm. The DNA/RNA can enter the cells/exosomes through the holes that made by the electric field.

(b) Lipofection.

The method commonly called transfection and can be used to transform cells/exosomes with DNA/RNA via vesicles containing the desired genetic constructs. The vesicles fuses with the cell membrane (similar to how two oil spots at the top of a broth will fuse) and the contents of the vesicles and the cells are combined. There are a number of transfection kits in the market, ready for use, e.g. DeliverX siRNA Transfection Kit (cat. No. DX0002) from Panomics, FuGENE® HD Transfection Reagent (Cat. no. 04709691001) from Roche and LIPOFECTAMINE™ 2000 (Cat. No. 11668-027) from Invitrogen.

(c) Transformation Using Heat Shock.

Chilling cells/exosomes in the presence of divalent cations such as $Ca^{2+}$ (in $CaCl_2$) makes their membranes become permeable to RNA or DNA plasmids/fragments fragments. Cells/exosomes are incubated with the DNA and then briefly heat shocked (42° C. for 30-120 seconds), which causes the DNA to enter the cell. This method works well for circular plasmid DNAs.

The above methods describe briefly how genetically modified exosomes can be achieved to transfer RNA and DNA to recipient cells. Exosomes that contain RNA/DNA or that are modified to contain the gene of interest will be isolated and shifted to the recipient cells, to affect their biological function or survival. Consequently, the exosomes will dispose their content into the cytoplasm of the target cells, which in turn leads to translation of mRNA to specific proteins in the target cell through the cells own protein machinery. Further exosomes are capable to carry and transfer small coding and none coding RNA such as microRNA and siRNA that may regulate translation of a specific gene.

Exosomes being vesicles as carrier of DNA or RNA as described in the invention herein can be used to treat inherited diseases in hematopoietic, non-hematopoietic, stem cells, and organs. Exosome vesicles can also be used as carriers of DNA or RNA constructs for treatments of microbiological infections or diseases or dysfunctions in humans or animals, or transfer of genetic material of any biological membrane.

Because in humans CD4 T-cells are the target for HIV infections, infected cells can be treated with RNA or DNA constructs (siRNA, RNAi, or DNA) carried and transferred by exosomes to the infected T-cells, specifically designed for silencing of the translation of the viral RNA. Thus our invention discloses that exosomes that are capable of transferring their nucleic acids to CD4 T-cells can be used for treatment of HIV infected T-cells, as well as T-cell malignancies such as lymphoma or lymphatic leukemias.

Changing or modifying the genetic material of exosomes by altering the condition for the exosome-producing cells, is achieved by changing pH, temperature, growing conditions, or using antibodies/chemicals toward exosome-producing cells. This results in alteration of the nucleic acid content. Also, over-expression or repression of cytokines, chemokines and other genes in the exosome-producing cells can be used to change or modify the genetic content of exosomes Transferring sense or anti-sense RNA to specific cells using exosome vesicles to switch off genes instead of adding new ones results in down regulation (slow down) or prevention of translation of the particular gene. The method is called RNA interference (siRNA).

The invention herein makes it possible to transfer genetic materials in vitro to stem-cells acquired from a patient or a donor prior to administration of this stem cell to a patient or a recipient human, or animal.

To administer nucleic acids to recipient cells or tissues, DNA or RNA-containing exosomes can be administered to cells by addition of the exosomes to cell cultures in vitro, or injection of these exosomes intravenously, or by any other route, in vivo as is known in the art. Exosomes can be targeted to any cell in the body, including cells in the cardiovascular system, skeletal muscle cells, joint cells, neural cells, gut cells, lung cells, liver cells or kidney cells, or cells in the immune system, or to any type of cell with any function or dysfunction in the body of humans or animals, including malignant cells.

As disclosed in the invention herein, exosomes can be used to deliver genetic material to recipient cells to use the cell's own protein machinery to produce any drug or precursor of any drug, or to affect the function or metabolism of any drug, in any cell in humans or animals.

To avoid interference with undesirable or irrelevant genetic material, it is preferable to use exosomes that are lacking genetic contents. Empty exosomes can be used for direct transfer to recipient cells or for direct transfection/ transformation of a specific gene (RNA or DNA) into exosomes.

Detection of Mast Cell Derived Exosomes.

Exosomes released from the murine mast cell line MC/9 (ATCC Manassas, Va., USA, Number: CRL-8306) were isolated, adsorbed to carbon-coated grids, and detected using electron microscopy. For detection of the exosome specific surface protein CD63, exosomes were also purified from both primary bone marrow mast cells (BMMC) and the cell line MC/9. The exosomes were adhered onto aldehyde beads and stained with a CD63 antibody followed by a secondary PE-coupled antibody. These beads were analysed using flow cytometric detection, confirming the presence of CD63 on the surface of both BMMC and MC9 derived exosomes.

Identification of Exosomal Proteins.

To understand the biological function of the mast cell derived exosomes, the protein content was analysed using nano-flow LC-MS/MS. The total protein content was extracted from the isolated exosomes and collected on a SDS-PAGE gel. The protein band was trypsinated and analysed by LC-MS/MS. The results of all the tandem mass spectra were searched by the MASCOT (Matrix Science, London) program for identification. The results revealed that these exosomes contain a larger number of proteins than were previously known. Approximately 150 proteins were identified, many of which are associated with cellular transcription, translation, and protein folding. The identified proteins include several ribosomal proteins as well as heat shock proteins, chaperones, annexines, cytoskeleton proteins and membrane-bound proteins such as CD63, CD54, CD43 and MHC class I.

Detection of DNA and RNA from Mast Cell Derived Exosomes.

Since a certain number of the identified proteins are associated with RNA and the transcriptional machinery, we hypothesised that exosomes may also contain DNA and/or RNA. To examine this, we performed RNA and DNA extraction from both exosomes and the full exosome producing mast cells. Presence of DNA and RNA were determined by spectrophotometry and on an agarose gel. No DNA could be detected in the exosome sample, whereas a substantial amount of selective RNA was observed from the exosomes. Specifically exosomal RNA contained very low, or undetectable, amounts of ribosomal RNA, which indicates the presence of other types of RNA, i.e. mRNA.

Microarray Analysis of Exosomal RNA.

In order to characterize the RNA from the mast cell derived exosomes, Affymetrix mouse DNA microarray (Affymetrix) was applied using RNA from both mast cells and their exosomes. The results revealed that exosomes carry mRNA from approximately 2500 genes, which is approximately 10% of genes that are expressed in the mother mast cells. Furthermore, the gene profile analysis displayed essential differences in the mRNA between the exosomes and their parental cells. The most abundant transcripts in the exosomes differ from abundant transcripts in the parental cells which indicate selectivity of the exosomal RNA. Interestingly, the exosomes carried mRNA from 180 genes whose transcript were absent in their mother mast cells. The results indicate that mRNA is transported into exosomes in a highly selective way and it seems that the parental cells express a certain number of genes exclusively for exosomal delivery.

Detection of RNA from BMMC Exosomes.

To identify RNA in exosomes from a non-cell line source, bone marrow cells were harvested from mice and cultured to become mast cells (Bone Marrow derived Mast Cells: BMMC) for 4 weeks. During the last 48 hours, the cells were cultured in the presence of radioactive uracil (see example 1). The exosomes from the culture were isolated and the RNA labelled with radioactivity was detected by scintillator counting. The results showed that the incorporated radioactive uracil in cellular RNA could be found in exosomes. The amount of RNA from the bone marrow derived exosomes is not as abundant as in the mast cell line exosomes, which can be explained by a lower number of BMMC cells used for the harvest, and the in vitro growth condition of these cells.

Transfer of RNA by Exosomes Between Cells.

In order to examine whether exosomes can transfer the mRNA they contain to another cell, mast cell derived exosomes containing radioactive uracil mRNA were added to cultured dendritic cells (DC), CD4 T-cells, and MC/9 mast cells. Samples from the cultures were taken at different intervals and the cells were isolated and washed by centrifugation. RNA from the recipient cells was isolated and examined for radioactive uracil using a scintillator. Most importantly, DC, CD4 and MC/9 cells exposed to the exosomes contained increased amount of radioactive uracil, thus having been absorbed from the exosomes. The results show that mast cell derived exosomes can transfer RNA to other cells, in this case DC, CD4 and MC/9 cells.

The data show that mRNA can be transferred between two mammalian cells through exosomes. Biologically, this suggests that one cell can affect another cell's protein production by signalling via exosomes. This has substantial biotechnological applications, since exosomes may be used as carriers to deliver mRNA, or DNA-probes, to target cells such as malignant cells or cells in the immune system. Therefore according to this invention, the exosomes provide a vehicle for gene modulation and therapy that is likely to be without the side effects of other gene therapy vehicles, such as viruses or other types of lipid bodies.

The features of the present invention will be more clearly understood by reference to the following examples, which are not to be construed as limiting the invention.

EXAMPLE 1

Cell Preparation

MC/9 cells (ATCC) were cultured according to manufacturer's recommendations. To eliminate exosomes present in serum, Rat T-Stim and FBS were ultracentrifuged at 120,000 g for 90 min using a Ti70 rotor (Beckman optima LE-80k Ultracentrifuge). The human mast cell line HMC-1 (Dr Joseph Butterfield, Mayo Clinic, USA), was cultured in IMDM containing 10% FBS, 100 U/ml penicillin, 100 µg/ml streptomycin, 2 mM L-glutamine and 1.2 mM alph-thio-glycerol. For release of exosome, the HMC-1 cells were cultured in the presence of 1 µM calcium ionophore for 30 min. Bone marrow mast cells (BMMC) were prepared by culturing bone marrow cells from femurs of 7-10 wk old male BALB/c in the presence of IL-3 (R&D systems) as described previously (Razin, E. et al. Interleukin 3: A differentiation and growth factor for the mouse mast cell that contains chondroitin sulfate E proteoglycan. *J Immunol.* 132, 1479-1486 (1984)). After 4 weeks of culture, the cells were harvested and consisted of 96% pure MCs as analysed by morphology. During the last 48 h, BMMC were cultured at $3 \times 10^6$ cells/ml in complete medium with ultracentrifuged FBS supplemented with 10 ng/ml IL-4 (R&D-systems), and in some experiments in the presence of 1 µl/ml $^3$H-Uracil (Amersham Biosciences). For culture of CD4$^+$ T cells, mouse spleens were collected and passed through a 70 µm followed by 30 µm filter. CD4$^+$ T cells were purified by negative selection using the SPINCEP® mouse CD4$^+$ T cells enrichment cocktail (Stemcell Technologies) according to the manufacturer's instructions. The purity of the CD4$^+$ T cells ranged from 89 to 91%, as analysed by flow cytometry. The cells were cultured in RPMI 1640 containing 10% FBS, 100 U/ml penicillin and 100 µg/ml streptomycin at $1 \times 10^6$ cells per ml in flat bottom 48 well plates.

EXAMPLE 2

Exosome Purification

Exosomes were prepared from the supernatant of MC/9, BMMC and HMC-1 cells by differential centrifugations as previously described (Raposo, G. et al. B lymphocytes secrete antigen-presenting vesicles. *J. Exp. Med.* 183, 1161-1172 (1996)). Cells were harvested, centrifuged at 500 g for 10 min to eliminate cells and at 16,500 g for 20 min, followed by filtration through 0.22 µm filter to remove cell debris. Exosomes were pelleted by ultracentrifugation (Beckman Ti70 rotor) at 120,000 g for 70 min. For mass spectrometry, the exosome pellet was washed once in PBS. Exosomes were measured for their protein content using BCA™ Protein Assay Kit (Pierce). For the density gradient experiment the 120,000 g exosome pellet was floated in a sucrose gradient (0.25-2 M sucrose, 20 mM Hepes/NaOH, pH 7.2). The exosomes were dissolved in 2.5 M sucrose and the gradient was layered on top of the exosome suspension. The gradient was centrifuged at 100,000 g for 15 h according to (Rapso et al 1996). Briefly, the gradient fractions (10×3.8 ml) were collected from the bottom of the tube, diluted with 10 ml PBS and ultracentrifuged for 2 h at 150,000 g (Beckman Ti70.1 rotor), and the pellets were extracted by Trizol® (Invitrogen).

EXAMPLE 3

Isolation of RNA, DNA and Proteins

RNA, DNA and proteins were isolated using Trizol® (Invitrogen) or RNEASY® mini kit (Qiagen) according to the manufacturer's protocol. For co-purification of microRNA and total RNA, the RNA was extracted using Trizol, followed by the RNEASY® mini kit. Cells and exosomes were disrupted and homogenized in Buffer RLT (Qiagen) and 3.5 volumes of 100% ethanol were added to the samples prior use of the RNEASY mini spin column. The rest of the procedure was performed according to the manufacturer's protocol.

EXAMPLE 4

Introducing DNA/RNA Fragments or Constructs into Exosomes

Insertion of Specific Constructs Directly into Exosomes.

Exosomes can be isolated from different origin, e.g. in vitro growing cells, human body, or cells originated from a human and animal. Genetic constructs of RNA or DNA can be introduced into these exosomes directly by using conventional molecular biology techniques such as in vitro transformation, transfection, and microinjection.

EXAMPLE 5

Administration of DNA or RNA-Containing Exosomes to Cells

Transfer Experiments

To label MC/9 exosome RNA, cells were cultured in complete medium supplemented with 1 µl/ml $^3$H-Uracil 72 h before exosome isolation. Exosomes were isolated according to the isolation protocol and washed by ultra-filtration (10 kDa, Millipore) to remove free nucleotides. The exosomes were added to MC/9, CD4$^+$, and HMC-1 cells in the ratio of 8:1 between donor cells and recipients at the starting point of labeling. At 0 h and 24 h, cells were harvested and washed twice. RNA was isolated by RNEASY® mini kit and the signal of radioactive RNA was measured using scintillation. Medium supplemented with 1 µl/ml $^3$H-Uracil absent from donor cells was treated equally and used as negative control.

In Vitro Translation

Total exosomal RNA was purified using RNEASY® mini kit and 0.5 µg was used for the translation. The in vitro rabbit lysate translation kit (Promega Corporation) was used according to the manufacturer's recommendation to translate exosomal mRNA to proteins. A sample without exosomal RNA was treated equally and used as negative control. After the translation procedure was accomplished, total proteins were precipitated using acetone and determined using RC DC protein assay (BioRad). The protein content of the samples (presence and absence of the exosomal RNA) was compared using 2D-PAGE, BioRad instruments (Mini-Protean® 3cell) and recommendation. The 2D-gels were visualized using SyproRuby (BioRad) and digitalized using phosphoimager. Protein spots of the samples were compared and a selection of the newly produced proteins was cut, trypsinated, and identified using LC-MS/MS followed by MASCOT program search. The newly produced proteins of mouse origin were compared to the genes identified from the DNA microarray analysis.

In Vivo Translation

MC/9 exosomes (1000 µg) were added to HMC-1 cells ($8 \times 10^6$) in three different time points (0, 3, 6 h) and the cells were incubated for approximately 24 h. The HMC-1 cells were harvested, washed, and the total proteins of the cells were separated by 2D-PAGE according to Proteomics Core facility. A sample without exosomes was treated equally and used as negative control. The newly produced proteins were detected using PDQUEST and 96 spots were cut and identified using MALDI-tof followed by MASCOT program search, according to Proteomics Core Facility (University of Gothenburg).

The exosomes then deliver the nucleic acids to recipient cells and consequently affect their biological function or survival.

EXAMPLE 6

Production of Exosomes that are Lacking Genetic Material

The empty exosomes are used for direct transfer to recipient cells or for direct transfection/transformation of a specific gene (RNA or DNA) into exosomes. The methods to produce empty exosomes (empty of genetic material) are multiple as known by one skilled in the art; including UV-exposure, mutation of proteins that carry RNA into exosomes, as well as electroporation and chemical treatments to open pores in the exosomal membranes. The methods include mutation/deletion of any protein that can modify loading of any nucleic acid into exosomes.

EXAMPLE 7

Production of Mouse Proteins in Human Mast Cells after Transfer of Mouse MC/9 Exosomes To test whether mouse proteins could be produced in human mast cells after transfer of mouse MC/9 exosomes, we determined the presence of mouse proteins in the recipient cell, by 2D-PAGE followed by MALDI-tof. After incubation of the human cells with mouse MC/9 exosomes for 24 hours, 96 new or enhanced protein spots were identified. Interestingly, three distinct mouse proteins were identified in the human cells that are not present in MC/9 exosomes. These proteins were mouse CDC6 (O89033), mouse Zinc finger protein 271 (P15620) and mouse CX7A2 (P48771). The mRNA of the first two proteins was present in two of the microarray experiments, and the last one was present in all four microarrays performed, suggesting that mRNA delivered by exosomes to a recipient cell can be translated to proteins.

The proteomic results from transfer of MC/9 exosomes to HMC-1 cells when human mast cells HMC-1 were incubated with the mouse MC/9 exosomes and without for 24 hours show that mouse proteins could be produced in the human mast cells. Proteins between the two gels were matched and 96 newly produced proteins were identified by MALDI-tof and mouse proteins were produced from the exosomal mRNA.

EXAMPLE 8

Using Exosomes as Gene Therapy of Malignant Disease

Exosomes are produced by malignant cells, taken from a patient suffering from a malignant disease. These exosomes are processed to contain genetic constructs of any type or specificity, to be reintroduced to the patient. The exosomes from the malignant cell then preferentially fuse with cells of the same type, which deliver the DNA and or RNA constructs to the malignant cell specifically, as gene therapy of malignant disease. The procedure is performed according to example 1-6, but with exosomes produced by malignant cells.

While the invention has been described with reference to specific embodiments, it will be appreciated that numerous variations, modifications, and embodiments are possible, and accordingly, all such variations, modifications, and embodiments are to be regarded as being within the spirit and scope of the invention.

What is claimed is:

1. A method of transferring genetic material to recipient cells, the method comprising:
    a) isolating exosomes produced and released by a donor mast cell, wherein the isolating is performed in vitro and the isolated exosomes lack genetic material;
    b) transforming, transfecting, or microinjecting selected genetic material to the isolated exosomes in vitro to produce modified exosomes; and
    c) administering the modified exosomes to recipient cells thereby transferring the selected genetic material from the modified exosomes to the cytoplasm of the recipient cells.

2. The method of claim 1, wherein the selected genetic material is selected from the group consisting of mRNA, tRNA, rRNA, siRNA, regulating RNA, non-coding and coding RNA, DNA fragments, and DNA plasmids.

3. The method of claim 1, wherein the recipient cells are selected from the group consisting of cells from recipients having malignant diseases in hematopoietic or non-hematopoietic cells, or diseases in stem cells or organs.

4. The method of claim 1, wherein the selected genetic material comprises nucleic acids and the recipient cells comprise CD4 T-cells for treatment of HIV infected T-cells.

5. The method of claim 1, wherein the selected genetic material is transferred to treat diseases, induce or repress cell death, change cellular ageing, induce tolerance, re-direct existing immune responses, or change intracellular activity or cellular behavior.

6. The method of claim 1, wherein the selected genetic material is selected from the group consisting of mRNA, tRNA, siRNA, regulating RNA, non-coding and coding RNA, DNA fragments, and DNA plasmids.

7. The method of claim 1, wherein the donor mast cell is a genetically modified donor mast cell.

8. The method of claim 7, further comprising genetically modifying the donor mast cell to erase production of a nucleic acid, or to up-regulate or down-regulate production of a nucleic acid.

9. The method of claim 1, wherein the modified exosomes are administered to the recipient cells by a method selected from the group consisting of addition of the exosomes to recipient cell cultures in vitro, intravenous injection of the exosomes, in vivo administration of the exosomes to a patient comprising the recipient cells, and administration targeted to particular cells in a subject.

10. The method of claim 1, wherein the isolated exosomes are from mast cells from a patient with a malignant disease; and the modified exosomes are administered to the patient.

11. The method of claim 1, wherein the recipient cells comprise CD4 T-cells.

12. The method of claim 1, wherein the selected genetic material comprises DNA constructs.

13. The method of claim 7, wherein the donor cell is isolated from a person with human immunodeficiency virus (HIV).

14. The method of claim 9, wherein the modified exosomes are administered to the recipient cells by addition of the exosomes to recipient cell cultures in vitro.

15. The method of claim 9, wherein the modified exosomes are administered to the recipient cells by in vivo administration of the exosomes to a subject comprising the recipient cells.

16. The method of claim 9, wherein the modified exosomes are administered to the recipient cells by targeting particular cells in a subject for administration.

17. The method of claim 1, wherein the isolating comprises centrifugation and filtration of the donor mast cells.

18. The method of claim 1, wherein
the isolating comprises isolating exosomes from the donor mast cell via centrifugation and filtration;
the transforming, transfecting, or microinjecting comprises transforming the isolated exosomes via electroporation with a DNA construct to produce modified exosomes; and
the administering comprises administering the modified exosomes to recipient cells via co-incubation of the modified exosomes and recipient cells in tissue culture, thereby transferring the DNA construct to the cytoplasm of the recipient cells.

19. The method of claim 1, wherein
the isolating comprises isolating exosomes via centrifugation and filtration from the donor mast cells from a patient with a malignant disease;
the transforming, transfecting, or microinjecting comprises transforming the isolated exosomes via electroporation with a DNA construct designed for silencing of viral RNA translation to produce modified exosomes; and
the administering comprises administering the modified exosomes to recipient CD4 T-cells via co-incubation of the modified exosomes and recipient CD4 T-cells in tissue culture, thereby transferring the DNA construct to the cytoplasm of the recipient CD4 T-cells.

\* \* \* \* \*